United States Patent [19]

Schneider et al.

[11] Patent Number: 5,312,615
[45] Date of Patent: May 17, 1994

[54] INJECTABLE OPACIFYING COMPOSITION CONTAINING LIPOSOMES OF HIGH ENCAPSULATION CAPACITY FOR X-RAY EXAMINATIONS

[75] Inventors: Michel Schneider, Troinex; Hervé Tournier, Valleiry, France; Bernard Lamy, Carouge, Switzerland

[73] Assignee: Bracco - Industria Chimica S.p.A., Milan, Italy

[21] Appl. No.: 302,690

[22] PCT Filed: May 16, 1988

[86] PCT No.: PCT/EP88/00447
§ 371 Date: Jan. 19, 1989
§ 102(e) Date: Jan. 19, 1989

[87] PCT Pub. No.: WO88/09165
PCT Pub. Date: Dec. 1, 1988

[30] Foreign Application Priority Data
May 22, 1987 [CH] Switzerland ............... 1991/87

[51] Int. Cl.5 .............. A61K 49/04; A61K 49/00
[52] U.S. Cl. ................................. 424/5; 424/9
[58] Field of Search ............................. 424/5, 9

[56] References Cited

U.S. PATENT DOCUMENTS

| | | | |
|---|---|---|---|
| 4,192,859 | 3/1980 | Mackaness et al. | 424/5 |
| 4,599,227 | 8/1986 | Dees et al. | 424/450 |
| 4,647,447 | 3/1987 | Gries et al. | 424/9 |
| 4,744,989 | 5/1988 | Payne et al. | 424/5 |

FOREIGN PATENT DOCUMENTS 2437831 4/1980 France .

OTHER PUBLICATIONS

Chemical Abstracts: (106:125855w) 1987.

Primary Examiner—Frederick E. Waddell
Assistant Examiner—K. Weddington
Attorney, Agent, or Firm—Cushman, Darby & Cushman

[57] ABSTRACT

Injectable aqueous composition intended for opacifying certain organs with a view to examination by X-rays. This composition is based on liposomes containing, encapsulated therein, an aqueous solution of an iodinated opacifying agent. The ratio between the weight of iodine encapsulated by the liposomes and the weight of the lipids from which their membrane is formed is not lower than 1.5 mg/mg.

7 Claims, No Drawings

INJECTABLE OPACIFYING COMPOSITION CONTAINING LIPOSOMES OF HIGH ENCAPSULATION CAPACITY FOR X-RAY EXAMINATIONS

The present invention relates to an aqueous composition which can be injected into the circulatory system of a patient and the purpose of which is to opacify certain organs with a view to their diagnostic examination with X-rays. This composition is formed of a suspension, in a physiologically acceptable aqueous medium, of liposomes as vesicles with a phospholipidic membrane containing, encapsulated in these vesicles, an aqueous solution of at least one iodinated compound which is opaque to the X-rays.

It is known to use suspensions of liposomes as vehicles for the transportation, in certain organs which are to be studied, of opacifying agents intended for radioscopic examinations. Thus, the specification of U.S. Pat. No. 4,192,859 describes such a suspension of liposomes constituted of lecithin and sterols and containing about 20 to 60% by weight of a contrast agent intended for the examination of organs, particularly of organs in relation with the reticuloendothelial and cardiovascular systems, as well as lymphographic examinations. Among such contrast agents, the following compounds are referred to in this specification:

N,N'-bis[2-hydroxy-1-(hydroxymethyl)-ethyl]-5-[(2-hydroxy-1-oxopropyl)-amino]-2,4,6-triiodo-1,3-benzene-dicarboxyamide (iopamidol); metrizamide; diatrizoic acid; sodium diatrizoate; meglumine diatrizoate; acetrizoic acid and its soluble salts; diprotrizoic acid; iodamide, sodium iodipamide, meglumine iodipamide, iodohippuric acid and the soluble salts thereof; iodomethamic acid; iodopyracetiodo-2-pyridone-N-acetic acid, 3,5-diiodo-4-pyridone-N-acetic acid (Iodopyracet); the diethylammonium salt of the preceding acid; iothalmic acid; metrizoic acid and the salts thereof, the ipanoic, iocetamic, iophenoxic acids and their soluble salts; sodium tyropanoate, sodium iopodate and also other similar iodised compounds. The lipidic membrane of the liposomes which are used in accordance with this document mainly contains phospholipids, a sterol, lecithin, dicetyl phosphate or stearyl amine, and an organic solvent. Always in accordance with this document, it is possible to prepare such liposomes by the selected lipidic components being mixed in a container with an organic solvent, such as chloroform, dichloromethane, ethyl ether, carbon tetrachloride, ethyl acetate, dioxane, THF, etc. After having evaporated the volatile compounds under reduced pressure, the lipidic mixture is dispersed in a buffering solution containing a measured quantity of an opacifying agent. The whole is then stirred for several hours, this causing the formation of liposomes, a part of the dispersion liquid (containing the opacifying agent) then being encapsulated in the liposomic vesicles which are thus produced. The dispersion is then subjected to a sonication in order to reduce the size of these liposomes and the viscosity of the dispersion.

There are other documents which are concerned with the preparation of liposomes which contain opacifying agents.

For example, the specification of FR-A-2,561,101 describes a process for the preparation of liposomes which may contain X-ray opacifying agents. According to this specification, there are first of all prepared "precursors" of liposomes in organic solution, from which then the solvent is partially separated, this solution containing a proportion of lipids which are adapted to convert the monomolecular membrane of the precursors into bimolecular membrane. This solution is then dispersed in an aqueous medium and the residual solvent is completely eliminated.

The specification of U.S. Pat. No. 4,567,034 describes X-ray opacifiers and the incorporation thereof into the liposomes as vector of a contrast product.

The specification of GB-A-134,869 describes a technique for the preparation of liposomes, in accordance with which particles (10 $\mu$m) of a hydrosoluble carrier agent (NaCl, saccharose, lactose, etc.) are coated with an amphipatic agent, the subsequent dissolution of the carrier in an aqueous medium yielding the liposomes. The coating is effected by dispersing the solid particles of the carrier in an organic solution of the lipid and of the product to be encapsulated, among which are found the X-contrast agents. Among the amphipatic agents, there are to be mentioned the saturated synthetic lecithins.

The specification of GB-A-2,135,268 also describes a process for forming liposomes which may contain opacifiers, starting from particles of a hydrosoluble carrier agent.

The specification of GB-A-2,135,647 describes a process for the preparation of liposomes which are somewhat similar to that of the two preceding documents, except for the difference that the particles of the carrier material are insoluble. What are involved here are microspheres of glass or synthetic resin. These particles are coated with a film containing a lipid and, optionally, an ionic surfactant or chloesterol, by bringing them into contact with an organic solution of these ingredients, the operation being followed by an evaporation. Thereafter, by agitating these spheres in an aqueous dispersion medium to be encapsulated, more particularly containing an X-ray opacifier, then separating out the latter by filtration or centrifugation, there is obtained the desired solution of liposomes.

The specification of GB-A-2,156,345 describes diacetylaminated compounds of triiodobenzoic acid as X-contrast agents and the incorporation thereof into liposomes.

The specification of GB-A-2,157,283 describes compounds which are similar to those of the preceding document and the incorporation thereof, in amounts of 20-60%, into liposomes. The latter are in conformity with the preparation which is described in the specification of U.S. Pat. No. 3,957,971.

The specification of EP-A-179,660 describes a process for preparing suspensions of liposomes, in accordance with which a bioactive substance to be encapsulated is dispersed in the presence of lipids in organic solution, the solvent is evaporated until there is formation of a gel and this latter is redispersed in a second buffering aqueous medium. By a suitable control of the respective quantities of the ingredients and of the operating conditions, this results in a very high degree of encapsulation and a very uniform distribution of the liposomic vesicles.

Among other recent documents which are concerned with liposomes, as vectors of contrast products, they may also be mentioned: A. HARVON et al. Radiology (1981) 140, 507; P. J. RYAN et al., Biochim. Biophys. Acta (1983), 756, 106; S. E. SELTZER et al., AJR (1984) 143, 575; P. J. RYAN et al., Radiology (1984)

152, 759; O. A. ROZENBERG, Radiology (1983) 149, 877; S. BENITA et al., J. Pharm. Sci (1984) 73, 1751; K. T. CHENG et al., Investigative Radiology (1987) 22, 47-55; M. R. ZALUTZKY et al., Investigative Radiology (1987) 22, 141-147.

Although the said art disclosed in the aforementioned documents performs well in experimental tests, certain practical problems as regards utilisation remained to be resolved.

Thus, although the liposomic vesicles containing an opacifying agent are finally fixed in the liver and the spleen, it is also possible for them, with their displacement in the circulatory system, to be retained by the capillaries of the lungs with the risk of fatty embolism. Moreover, the specific capacity of encapsulation by volume and weight of iodinated products of the actual liposomes is relatively small (usually less than 1 g of iodine per g of lipids), and this necessitates the injection of a relatively large quantity of lipids in order to achieve the desired opacifying effect. On this subject, it is noted that, in practice, it is customary to characterize a preparation of liposomes by the amount of encapsulated iodine as g of iodine per g of lipids (ratio I/l), although obviously this iodine is bonded to an organic molecule. As regards the quantity of iodine necessary for an examination using X-rays, it is admitted that the opacification of the liver requires a concentration of the order of 2-2.5 mg of iodine per g of tissue, i.e. about 6 g (weight of liver about 2.3 kg). Taking account of the fact that only about 40% of the injected liposomes are retained in the liver, it is therefore necessary for a minimum of 15 g of iodine to be administered. For a ratio I/l of 1 (a high value in the state of the art) this corresponds to 15 g of lipids, which constitutes an already considerable dose. It is seen from this that the major interest is to increase the encapsulation capacity of the liposomes.

By way of example, it is noted that, according to V. J. CARIDE, in CRC Critical Reviews in Therapeutic Drug Carrier Systems (1985), 1. 121-153, the encapsulation capacity of liposomes of the class which he defines as "small unilamellar vesicles, (SUV), which have a diameter between 0.02 and 0.5 μm, is of the order of 0.2 to 1.5 l/mole, which corresponds, admitting a mean molecular weight of about 800 (phospholipids), to an encapsulation capacity of about 1 to 2 ml/g of phospholipids. Now it is desirable to raise this capacity to 5 ml/g or more, if possible, so that the ratio I/l, for example, when encapsulting opacifying solutions of the order of 300 mg of iodine/ml, may exceed the value of 1.5.

Moreover, an appreciable part of the iodine which is contained by the present suspensions of liposomes with opacifying capacity is dissolved in the aqueous dispersion phase and not encapsulated within the vesicles (see, for example, the suspensions described in the specification of U.S. Pat. No. 4,192,859). Such a situation may be found to be undesirable because, at the time of injection for diagnostic purposes, the portion of non-encapsulated iodine is not fixed in the organs to be investigated and does not serve any useful purpose. Consequently, in order to avoid having to inject iodine for nothing, it is desirable to be able to decrease as far as possible this non-encapsulated fraction.

The composition as defined in the claim 1 permits the disadvantages of lack of encapsulation capacity to be overcome. Actually, during their experiments, the present inventors have established to their surprise that, in "normalising" the size of the vesicles of the solution of liposomes in a certain range of values, i.e. by eliminating, by sizing by extrusion, the major part of the vesicles with a dimension below 0.15 μm or exceeding 3 μm, and preferably by keeping the major part of the vesicles at a size which is between 0.2 and 1 μm, the amount of encapsulated iodine was increased in a significant manner. This effect is the result of an increase in the specific encapsulation capacity of the vesicles (i.e. the volume of encapsulated liquid in relation to the weight of the lipids of the vesicular membranes), it being possible, in certain cases for this ratio to reach 10-15 ml/g of lipid.

In addition, and constituting another unexpected element, the procedure of calibrating the liposomes has made it possible to obviate, to a considerable degree, the problem of the retention of the liposomes in the capillaries of the lungs, the proportion of such liposomes detectable in this organ decreasing considerably as soon as the large size liposomes, for example, exceeding 2 to 3 μm, have been eliminated. It will be specified here that, by normalisation, it is wished to state that, in accordance with the definitions relating to the standards of statistical distribution of the particles according to their size, the operation of normalization leads to a contraction of the said vesicle distribution curve; thus, in the present invention, the index of their polydispersity is not higher than 4 and, preferably, the size of more than 70% of the total number of vesicles of the solution of liposomes is between 0.2 and 2 μm. It will hereinafter be seen, in the section concerned with the preparation techniques, what is to be understood by polydispersivity index.

Because of the above discoveries and by an appropriate choice of the opacifying iodinated compounds dissolved in the encapsulated solution according to claim 1, it has been possible successfully to obtain the opacifying compositions according to claims 2, 3 and 11. Moreover, by subjecting such a solution to certain appropriate treatments (hereafter described), a large part of the iodine dissolved in the aqueous suspension phase has been successfully eliminated. It will also be noted that the viscosity of the composition according to the invention, which may, in certain forms of execution, be lower than 30 or of the order of 20 to 30 mP.s at 37° C., is clearly lower than that of the suspensions according to the prior art (for instance, the suspensions described in the specification of U.S. Pat. No. 4,192,859 may, for iodine contents of 60%, reach viscosities of several hundreds of mP.s.). It is in fact evident that the viscosity of the suspensions of liposomes decreases when the lipid level diminishes and that, to keep the I/l ratio constant, it is necessary to increase to the same extent the encapsulation capacity of these latter.

Furthermore, the presence of iodinated opacifying agents contributes also to raising the viscosity of the solutions (for example, an aqueous solution of iopamidol at 300 g of iodine per liter has a viscosity of 8.8 mP.s at 20° C. and 4.7 mP.s at 37° C.) and any diminution of the concentration of the iodinated compound in the dispersion medium of the liposomes will contribute to lowering this viscosity.

The lipidic membrane of the liposomes of the composition according to the invention may be constituted of the amphipatic compounds normally employed in the usual practice of liposomic suspensions. Such compounds are described in the aforementioned references. It is preferred to use phospholipids, such as the hydrogenated lecithins of soya (for example, the products NC-95H of Nattermann Chemie), dipalmitoyl phosphatidyl choline (DPPC), distearoyl phosphatidyl choline (DSPC), sphingomyeline (SM) dicetylphosphate (DCP), dipalmitoyl-phosphatidyl glycerol (DPPG) and dipalmitoyl phosphatidic acid (DPPA). Contrary to the usual practice in the sphere of liposomes (cf. the references cited in the introduction), it is preferred not to use cholesterol among the lipids employed in the present invention, this not being essential for their stabilisation. The proportion of lipids relatively to the dispersion buffering phase is generally of the order of 0.1 to 10%, preferably about 2 to 6%. The proportion of encapsulated liquid relatively to the lipids (ratio v/l) is not below 5 ml/g and may in exceptional cases reach 20 ml/g. Preferably, it is between 5 and 15 ml/g, and most frequently between 7 and 12 ml/g.

As iodinated organic compounds which are opaque to X-rays, it is possible to use most of the compounds known from the aforementioned references; however, certain opacifiers are more suitable than others as regards the effective encapsulation capacity of their aqueous solutions in the liposomic vesicles and the stability of these vesicles in storage. Actually, certain of the opacifying agents in solution are more difficultly encapsulated than others at the time of formation of the liposomes and, moreover, certain of them diffuse more easily than others outside the liposomic membrane, in storage or at the time of handling.

For these reasons, it is preferred to use, as opacifying agents, the ionic contrast means derived from triiodobenzoic acid, such as, for example, the sodium and/or meglumine salts of diatrizoic acid, and preferably the non-ionic contrast means, such as iopamidol or iomeprol, given as a non-limiting example. The contrast agents are used in aqueous solution form with a concentration which is between 100 and 450 g of iodine/l, preferably of 250 to 380 gI/l. With such solutions, and the composition according to the invention, there are obtained amounts of encapsulated iodine which may be up to 6 g of iodine/g of phospholipid.

In general, with the composition of the invention, the volume occupied by the liposomic vesicles represents about 5 to 60% of the total volume of the suspension and may, in certain special cases, exceed these values (up to 70-80%).

For preparing the composition according to the invention, i.e. for increasing the encapsulation capacity of the liposomic vesicles and, for example, to provide an aqueous suspension of liposomes, the vesicles of which have a phospholipidic membrane with a power of encapsulating an opacifying aqueous liquid greater than 1.5 g of iodine per g of lipid (I/l > 1.5), the procedure is to normalise the size of these vesicles, i.e. to select an important proportion of vesicles of which the size is contained within a given range and eliminate the others, or by some means, to transform these latter (the others) into new vesicles having dimensions which correspond to the chosen range. By the term "important proportion" in respect of the normalisation of the size of the liposomes, reference is made to the notion of polydispersivity factor P used when measuring the dimensions of particles and the distribution of these particles by diffraction spectroscopy (see instructions for using the COULTER Nano-Sizer apparatus (registered Trade Mark)-COULTER ELECTRONICS LTD., Great Britain). The scale of the values of P ranges between 0 and 10. A value of 1 corresponds to monodimensional particles. A value of 8, for example, indicates that the ratio of the dimensions between the largest and the smallest particles is about 4.

Moreover, the factor s, which permits to calculate the extent W of the distribution curve of the particles, i.e. the dimension range of the majority of them, according to the relation $W = sd_w$ (where $d_w$ is the size of the particles given by the apparatus) is provided by dividing P by 5 for the particles larger than 250 nm and by 4 for particles between 100 and 250 nm. In the present invention, reference is made to the value of the polydispersivity index P and it is admitted that, for values of P equal to or smaller than 4, the majority of the vesicles corresponds to the measured size.

Therefore, the process as claimed in claim 4 illustrates a means for arriving at a composition such as defined in claim 1. It has in fact been ascertained that these are the liposomes of which the majority of the vesicles have a size which is between about 0.15 and 3 μm, preferably 0.2 and 1 μm, which have a particularly high encapsulation capacity. By the term "majority", it is wished to express the fact that at least 70% of the liposomic vesicles have a diameter conforming to the chosen range.

Although the exact reason why the liposomic vesicles contained in this range have the capacity of integrating such a high volume has not been elucidated, it is possible to advance the following arguments. Firstly, the liposomes below this limit have an unfavourable volume/surface ratio (actually, the more the diameter of a sphere decreases, the smaller this ratio becomes) and secondly, the vesicles exceeding approximately 2 μm are often plurilamellar and consequently, the mass of their membrane, for a given capacity, is higher. It appears that, by extrusion through a correctly calibrated membrane, the plurilamellar liposomes are re-arranged, at least in part, into smaller liposomes having a monolamellar membrane; a large proportion of these "rearranged" liposomes then corresponds to the optimal dimensions suitable for the composition according to the invention.

Generally, the normalisation of a solution of liposomes is effected by being forced under pressure through a filtering membrane. The pressures brought into play by this "extrusion" may vary between a fraction of a bar and several bars. Preferably, for membranes having a porosity which is between about 0.4 and 2 μm, extrusion pressures from 0.5 to 10 bar are used. In this way, it is possible to assure filtration rates of the order of 1 to 20 ml/sec/cm². It is quite understood that the increasing of the I/l ratio following the extrusion treatment is produced when the aqueous dispersion phase contains an iodinated opacifying compound in an appreciable proportion. It is evident that if this phase is deprived of iodine, it is not possible to have an increase of the encapsulated iodine by passage of the exterior phase towards the interior of the vesicles.

It has been established that the extrusion temperature plays a part in connection with the concentration of opacifying agents of the solution encapsulated in the vesicles. Thus, if the extrusion is effected at normal temperature, it is possible to produce a certain diminution of the I/l ratio. On the contrary, and this constitutes an additional unexpected element, if one proceeds at a temperature higher than the transition temperature of the phospholipids forming the wall of the liposomes, there is observed an increase in this ratio. Preferably, temperatures between 50° and 90° are used, for example, in the region of 75° C. It may be imagined that the unexpected result which is observed is due to a softening of the vesicles, caused by the raising of the temperature.

For lowering as much as possible the quantity of nonencapsulated iodine contained in the suspension, i.e. the portion of opacyfing agent dissolved in the buffering aqueous phase in which the liposomes are suspended, ultracentrifugation or ultrafiltration have advantageously been used, these procedures causing a physical separation between the vesicles themselves and the said aqueous phase. Once this separation is achieved, the liposomes are redispersed in a new aqueous dispersion phase. By repeating this operation, it is possible to reduce the proportion of opacifying agent in the exterior medium to a chosen content, for example, of the order of 2 mg/ml or even 0.2 mg/ml, without the loss of liposome (inevitable with each operation) becoming considerable. In general, such centrifuging operations are conducted with centrifugal accelerations of several thousands of g, for example, between 10,000 and 250,000 g. It is also possible to obtain such results by microfiltration, or dialysis, in accordance with usual techniques. It is possible to effect microfiltration operations by causing circulation of the suspension to be treated in a set of tubes of which the wall has a determined controlled porosity, for example, pores of 0.1 $\mu$m and more (in the case of the previously mentioned ultrafiltration, the pores of the membranes are smaller than 0.1 $\mu$m). In proportion as the volume of the suspension subjected to the filtration decreases (by passage of a part of this suspension through the pores of the tubes), it is replaced by fresh solvent, for example, a buffering mixture or a physiologically acceptable aqueous solution. Using these techniques, most of the undesirable substances contained in the dispersion liquid, particularly the dissolved iodine, are eliminated. Furthermore, the microfiltration permits eliminating, in the filtrate, certain undesirable solutions, especially the very small residual vesicles, this having the effect of improving the I/l ratio.

As media constituting the exterior suspension phase of the liposomes, it is possible to use solutions which are compatible with the living tissues and the liquids of the circulatory system. To be mentioned as examples of such solutions are the salt solutions, aqueous solutions, buffered or not with Tris, phosphate, etc. (pH in the region of neutrality) and the hypertonic solutions containing one or more substances selected from salt, glucose, opacifying agents, buffering agents, etc. One typical solution (0.8 Osm) contains glucose (0.7M), NaCl (0.9%) and Tris (10 mM).

For the preparation of suspensions of liposomes capable of being used as starting products in the present invention, it is possible to use known techniques, particularly those described in the previously cited references.

Preferably used is the REV method (cf. F. Szoka et al., (1978), Proc. Natl. Acad. Sci. USA 75, 4194) and that described in the specification of EP-A-179.660.

By application of these methods, there are obtained initial suspensions of liposomes which, in general, have the following parameters: buffer 0.9% NaCl, 10 mM Tris, pH 7-7.5;
 lipids, about 1%
 total iodine concentration, 20-30 mg/ml;
  iodine concentration in the liposomes 1-2 g/g of lipids (solution of iopamidol at 300 g/l).

By subjecting such initial solutions to the aforementioned operations, there are obtained opacifying compositions in accordance with the invention.

As the time of its use as opacifying agent by injection into laboratory animals, the composition according to the invention is shown to be very effective, on account of its specific opacifying power and its selectivity. Particularly observed is a reduction by 30 to 40 times of the retention of iodine in the lungs. It is to be particularly noted that, with the present composition, using a total amount by weight of iodine smaller than 20%, it is possible to obtain diagnostic results equivalent or superior to those obtained with suspensions according to the prior art (see, for example, U.S. Pat. No. 4,192,859), wherein the global concentration of iodine may reach 60% by weight of suspension of liposomes.

The experimental part which follows illustrates the invention.

EXAMPLE 1

First of all, a solution is prepared which contains 57 mg of dipalmitoyl phosphatidic acid (DPPA, Fluka) and 543 mg dipalmitoyl phosphatidyl choline (DPPC, Fluka) in 42 ml of chloroform. To 20 ml of this solution are added 20 ml of chloroform and 40 ml of diisopropyl ether and then, after stirring, 12 ml of a 76% (p/v) aqueous solution of meglumine diatrizoate, an iodinated opacifying agent (Bracco). The mixture obtained, heated to 50° C., was subjected for 5 minutes to ultrasonics (Braun Labsonic 1510). The emulsion was then concentrated at 45° C. in a rotary evaporator until a gel was obtained. A mixture of about 8 ml of the 76% aqueous solution of meglumine diatrizoate and 4 ml of distilled water was then introduced into the flask and the evaporation was continued with rotation. After obtaining a homogeneous mixture, there was again added a mixture of about 20 ml of the solution with 76% of meglumine diatrizoate and 8 ml of distilled water and the last traces of solvents were eliminated by evaporation. The volume of the solution of liposomes as obtained (solution A) was adjusted to 40 ml by means of distilled water.

The quantity of meglumine diatrizoate effectively encapsulated within the liposomes was then determined. An aliquot of the preparation obtained (5 ml) was centrifugated for 25 minutes at 235,000 g. The vesicles were taken up in 10 ml of a saline solution (0.9% NaCl, 10 mM TrisHCl, pH 7.2) and then subjected to a second centrifugation operation (15 minutes, 26,000 g). These phases of centrifugation, followed by taking up in suspension, were repeated another four times, this making possible the complete elimination of non-encapsulated meglumine diatrizoate. After a last suspension in 5 ml, an aliquot of the solution obtained (0.9 ml) was added to 0.1 ml of a 10% solution of sodium dodecylsulphate and then heated to 40° C. for 5 minutes. By measuring the optical density at 260 nm of this solution, it was determined at this stage that the final preparation contained 21.4 mg/ml of meglumine diatrizoate, corresponding to 10.4 mg of iodine per ml. By disregarding the losses of lipids, it is established that this preparation would likewise contain 7.14 mg/ml of phospholipids, i.e. an iodine/phospholipids ratio of 1.45.

The remainder of the solution A was brought to 75° C., then extruded under heat through a polycarbonate filter (Nuclepore) with a porosity of 1 micron. The solution obtained was then cooled to ambient temperature and thereafter subjected to a series of centrifugations, followed by being taken up in suspension, as described above. Spectrophotometric analysis of the supernatant liquid obtained after the fifth washing showed a residual iodine concentration in the external phase lower than 0.2 mg/ml. At this stage, the residue of liposomes was suspended in a total volume of 7 ml of buffer. In order to determine the total concentration of iodine in the final preparation, an aliquot quantity of this preparation was incubated, as described above, for 5 minutes at 40° C. in the presence of sodium dodecyl-sulphate. Spectrophotometric analysis showed that the final preparation contained 128.5 mg/ml of meglumine diatrizoate corresponding to 62.5 mg of iodine per ml and presenting an I/L ratio of 1.75. The extrusion has thus led to an increase of 20% of the encapsulated iodine.

EXAMPLE 2

To 100 ml of diisopropyl ether were added 100 ml of a mixture of phospholipids containing the following substances, in parts by weight: DPPC 3/DPPA 1/DSPC 1, this mixture being dissolved in chloroform at the concentration (by weight) of 7.1 mg/ml.

There were then added 30 ml of a 61.2% aqueous solution of iopamidol (300 mg of iodine per ml) and the whole was then subjected for 6 minutes to a sonic treatment using ultrasonic waves at 50° (BRAUN Labsonic 1510 ultrasonic apparatus). The milky solution was then evaporated, using the Rotavapor (45°/8 mm Hg) in order to eliminate the volatile solvents. The gel as formed was re-dispersed in 100 ml of the iopamidol solution. Samples of this preparation were then subjected to extrusion tests through (Nuclepore) membranes of 0.8 µm, 1 µm or 2 µm at 75° C. under a pressure of about 5 bars.

The various extruded or non-extruded preparations were then subjected to ultracentifugation (235,000 g; 30 minutes), after which the liposomic vesicles were re-dispersed in a buffering medium (0.9% NaCl 10 mM Tris, pH 7.2) (Tests 1 and 2). According to a modification, there was used, as dispersion phase, an iso-osmolar medium to the iopamidol solution, i.e. formed of 0.7M glucose, 15 mM NaCl, 1 mM Tris (test 3). This purification step (elimination of the iodine dissolved in the dispersive phase) was then repeated a certain number of times with one or other of these solutions, the centrifuging taking place at 26,000 g for 15 minutes, down to a residual iodine content of the dispersion phase below 0.2 mg/ml. This content was measured by spectrophotometry at 260 nm. In general, a number of centrifugation and redispersion stages of four, or less, is sufficient for achieving the desired degree of purification.

As this stage, the quantity of encapsulated iodine was determined as described in example 1, by treatment of an aliquot quantity with sodium dodecyl-sulphate (SDS): 0.1 ml of 10% aqueous SDS is added to 0.9 ml of the solution of liposomes, and the mixture is heated for 5 minutes at 40° C., then the spectrophotometric reading is taken (the control being an identical sample without encapsulated iodine). The optical density corresponding to 1 µg of iodine/ml of solution is 0.054 at 260 nm. By means of a particle counter (COULTER Nanosizer), the mean size of the liposomic vesicles and also the polydispersivity thereof were established.

The results appear in the following table. The tests 1 and 2 concern samples of suspensions in a saline solution; the tests 3 concern suspensions in glucose medium.

| Test | Membrane porosity (µm) | Means size of vesicles (nm) | Polydispersivity | Encapsulated iodine (g/g of lipids) |
| --- | --- | --- | --- | --- |
| 1 | initial state | 610 | 5 | 2.23 |
| 1A | 2 µm | 555 | 5 | 2.49 |
| 2 | initial state | 662 | 5 | 3.02 |
| 2A | 1 µm | 482 | 4 | 3.75 |
| 2B | 0.8 µm | 468 | 3 | 3.81 |
| 2C | 0.8 µm (4 extrusions) | 346 | 3 | 3.75 |
| 3 | initial state | 919 | 5 | 3.61 |
| 3A | 2 µm at ambient temperature* | 708 | 3 | 3.12 |
| 3B | 2 µm at 75° C. | 883 | 3 | 3.96 |

*In this test, extrusion took place at ambient temperature instead of 75° C.

The results of this table show that a single extrusion operation leads to a significant increase in the amount of encapsulated iodine and a decrease of the polydispersivity index P. In addition, the I/l proportion of encapsulated iodine (and also the degree of homogenisation of the size of the vesicles) increases when the dimension of the pores of the filtering membrane decreases.

In other tests, it has been possible to increase the encapsulated iodine content up to about 6 mg/mg of lipids.

EXAMPLE 3

In accordance with E. SPONTON et al. (Intern. J. Pharmaceutics (1985) 23, 299), a solution was prepared which contains 543 mg of dispalmitoyl phosphatidyl choline (FLUKA), 57 mg of dipalmitoyl phosphatidic acid (FLUKA) and traces of $^{14}$C-tripalmitine (Amersham, 0.1 µCi) in chloroform (42 ml). 14 ml of this solution were placed in a 200 ml flask and evaporated to dryness in a rotary evaporator under a partial vacuum at 25° C. There were then added 25 ml of a 61.2% solution of iopamidol (BRACCO) (corresponding to 300 mg of iodine per ml) previously heated to about 55° C., and the mixture was allowed to incubate for two hours at ambient temperature. This mixture was then subjected to five centrifuging operations in succession (one at 235,000 g for 30 minutes, followed by four at 29,000 g for 30 minutes at 4° C.), each of these centrifuging operations being followed by the residue being resuspended in a saline solution (NaCl 0.9%, Tris-HCl 10 mM, pH 7.2). There was thereafter determined, spectrophotometrically at 260 nm (see the preceding example), the residual concentration of iopamidol in the washwaters of the last washing operation, and also that of the encapsulated solution after rupturing of the liposomic vesicles by sodium dodecyl-sulphate (SDS). In this way, there were measured 0.08 mg of iodine per ml in the residual washing waters, and 7.8 mg per ml of encapsulated iodine per ml of liposome solution in the washed composition (25 ml). By analysis, using a scintillation counter (Beckman LS 8100) of an aliquot quantity of the final composition (see example 4), it was established that the concentration of the lipids was 5.2 mg/ml (this corresponding to 65% of the initial lipids).

The preparation of the liposomes as described above was repeated so as to obtain, in total, 375 ml of suspension containing 7.7 mg of encapsulated iodine per ml and 5.5 mg of lipids per ml (ratio of iodine/phospholipids 1.39). This preparation was then subjected to a diafiltration at 10° C. with the aid of a microfiltration module (type MD 020 CP2N, porosity of 0.2 µm, ENKA, Wuppertal, German Federal Republic), the volume of liquid passing through the membrane and eliminated in the filtrate being continually replaced by addition in the suspension of liposomes of a fresh saline solution (NaCl 0.9%, Tris-HCl 10 mM pH 7.2). After elimination of 1.5 l of filtrate, the diafiltrateed solution was concentrated, this yielding 97 ml of microfiltered liposomes, the majority of the vesicles of a size smaller than 0.2 μm having been eliminated. Analysis shows that this preparation contains 24.9 mg of encapsulated iodine per ml and 16.4 mg of lipids per ml, i.e., a ratio of encapsulated iodine/phospholipids of 1.52. The microfiltration has thus made it possible to increase the encapsulated iodine/phospholipid concentration from 1.39 to 1.52, i.e. an increase of about 9%.

EXAMPLE 4

Solutions of liposomes (3 batch) were prepared by the technique which is described in example 2 from 120 mg of lipids (NC-95H/DPPA=9/1 by weight), these lipids also containing 1.5 μCi of $^{14}$C-tripalmitine (radioactive tracer element). Used as iodine solution (300 mg/ml) is a solution of 61.2% by weight of iopamidol in an 8 mM Tris buffering agent, pH 7.2, $10^{-3}$M disodium EDTA, this solution being filtered beforehand through filters of 0.45 μm.

Two of the suspensions of liposomes obtained by means of the aforesaid ingredients were extruded, at 75° C., through membranes which respectively have a porosity of 2 μm and 0.8 μm. The third solution (control) was not extruded. The three solutions, respectively labelled E-2, E-0.8 and T, were further purified by ultracentrifugation as described in Example 2, then being suspended in a salt solution (0.9% NaCl, 10 mM Tris, pH 7.2); centrifugation and resuspension being repeated 4 times. In this way, measured by analysis as described in example 2, there are obtained, in succession, the following respective values for mean dimension of the vehicles (polydispersivity) and content of encapsulated iodine in mg per mg of lipids:

|   |   |
|---|---|
| T | 521 nm(5); 2.39 |
| E-2 | 351 nm(3); 2.72 |
| E-0.8 | 323 nm(2); 2.53 |

These liposomes were injected into the caudal vein of laboratory rats (SPRAGUE-DAWLEY) at the rate of 120 mg of iodine per kg. One hour after injection, the animals were killed and the blood was collected in heparinized tubes, as well as the organs, livers and lungs, which, after having been dried and weighed, were burnt in an appropriate combustion apparatus (PACKARD oxidiser). The $CO_2$ produced by this combustion was collected and analysed by scintillation. The blood was also analysed after being brought into solution (aliquot quantities of 0.25 ml) in 1:1 (v/v) mixture of Soluene/isopropanol (1 ml) and decolorization by $H_2O_2$ (0.5 ml, 32%). The various samples had added thereto 10 ml of DIMILUME (scintillation liquid) and their radioactivity was measured by means of a BECKMANN LS-8100 scintillation counter.

The results, set out in the following table, are expressed as a percentage of the injected dose retained by the blood or the organs under examination (each result is a mean of 3 measurements).

| Specimen | Blood | Liver | Lung |
|---|---|---|---|
| T | 1.0 | 41.5 | 12.3 |
| E-2 | 1.6 | 43.2 | 0.5 |
| E-08 | 1.4 | 47.9 | 0.3 |

It is established, from the above results, that the homogenisation of the dimension of the vesicles between the size limits corresponding to the porosity range of the 0.8 and 2 μm membrane results in a considerable diminution of the capturing of these vesicles by the lungs.

EXAMPLE 5

As described in example 4 (specimen E-08), suspensions of liposomes were prepared, analysis of such suspensions having supplied the following values:

32.5 mg of lipids and 70.2 mg of iodine/ml of suspension, this corresponding to 2.16 mg of encapsulated iodine per mg of lipids.

The next step was the injection of this suspension into four groups of Sprague-Dawley rats (five animals in each group) at the rate of 250 mg of iodine per kg.

By way of comparison, equivalent quantities of iodine, but not encapsulated in liposomes, were injected into control rats.

The animals were killed, in groups, after 30 minutes, 1 hour, 4 hours and 24 hours and the blood was collected and conserved in heparinized tubes. The organs (livers, spleens, kidneys and lungs) were removed beforehand and weighed. Aliquot amounts of these organs were homogenized in 7 mM ammonia (5 ml) in order to determine the quantity of residual blood in accordance with the method described by MEIJER et al. (Clin. Chim. Acta (1962), 7, 638).

The quantity of iodine retained by the various organs referred to above was determined by X-ray fluorescence, using a PHILIPS PW 1410 apparatus with a Cr anode, voltage=50 KV; current=50 mA. The corrected results for the blood content appear in the following table and also comprise measurements carried out on untreated animals.

TABLE

| | μg of iodine/g of tissues | | | | |
|---|---|---|---|---|---|
| Time after injection (h) | liver | spleen | kidney | lungs | blood |
| untreated animals — | 0.12 | 0.19 | 0.06 | 0.12 | — |
| non-encapsulated iodine 0.5 | 190 | 18 | 530 | 110 | 170 |
| 1 | 180 | 11 | 380 | 48 | 46 |
| 4 | 90 | 8 | 33 | 13 | 1 |
| 24 | 1 | 1.5 | 0.8 | 1 | 0.2 |
| encapsulated iodine 0.5 | 2400 | 5900 | 300 | 300 | 600 |
| 1 | 2700 | 6600 | 280 | 200 | 100 |
| 4 | 2200 | 6200 | 60 | 160 | 7 |
| 24 | 800 | 3500 | 15 | 50 | 0.6 |

The above results show how the administration of the iodine via the liposomes favours its retention by the liver and the spleen and eventually its relatively slow elimination by way of the kidneys.

In order to demonstrate the considerable technical progress which is achieved by the present invention, it is of interest to show, side by side, the results which are obtained by the invention and those according to the prior art.

For establishing this state of the art, reference is made to certain of the references which are cited in the introduction. The comparison in question is achieved by reference to the table, in which are set out a series of parameters which are inherent in the liposome suspensions. The names of the authors of the references appear in the first column.

EXAMPLE 6

The liposomes which are prepared as described in example 4 (specimen E-08) were injected intravenously in the dosage of 250 mg of iodine/kg to Sprague-Dawley rats which had been subjected to a computerized tomographic examination of the liver, before and after the injection.

A Siemens Somatom 2 tomograph was used, the examination being undertaken under the following conditions:

matrix of 256×256
field of view 14 cm
thickness of examined layer 2 mm
scanning time 5 seconds
X-rays: 125 KV mAs 230

The images were recorded before the injection of the suspension of liposomes, then 5', 10', 15', 30', 60', 90', 2 h, 3 h and 4 h after the injection, and there was observed an increase in contrast of the liver, expressed in Hounsfield Units (HU), this increase being between 50% and 130% during the period which is between 30 minutes and 4 hours.

It should be noted that if, in the techniques disclosed in the previous examples, dicetyl-phosphate (DCP) or dipalmitoyl-phosphatidyl glycerol (DPPG) is used in place of DPPA for preparing the liposome vesicles, similar results are experienced.

TABLE

Properties of liposomes containing opacifiers to X-rays

| Inventors | Lipids | Opacifying agent ($mgI_2/ml$) | Ratio by weight iodine/lipid (g/g) | Encapsulated volume (ml/g) |
|---|---|---|---|---|
| HAVRON et al. | Soya lecithin cholesterol stearyl amine | Diatrizoate (370) | 0.14 | 0.4 |
| RYAN(1) et al. | Phosphatidyl choline/ cholesterol | Diatrizoate (146) | 0.9 | 6.2 |
| ZELTZER et al. | Lecithin/ cholesterol/ stearyl amine | Iosefamate | — | — |
| RYAN(2) et al. | Phosphatidyl choline/ cholesterol | Diatrizoate | 0.4 | 1 |
| ROZENBERG et al. | — | — | 1.5 | — |
| BENITA et al. | Soya lecithin/ cholesterol | — | 0.2 | 2.7 |
| CHENG et al. | Egg lecithin/ phosphatidyl glycerol/ cholesterol | Iohexol (+others) | 0.25 | 0.6 |
| ZALUTSKY et al. | Lecithin/ cholesterol/ stearyl amine | Diatrizoate or iotrol | — | — |
| INVENTION (Example type) | NC 95 H/ DPPA (soya lecithin) | Iopamidol (300) | 3–4 | 7–12 |

We claim:

1. Process for increasing the encapsulation capacity of an aqueous suspension of liposomes comprising lipidic membrane vesicles containing, in encapsulated form, at least one opacifying agent to X-rays in solution in an aqueous liquid, wherein these liposomes in suspension in the said aqueous liquid are subjected to an extrusion through a filtering membrane with porosities ranging between 0.4 and 3 µm, so as to "normalize" the size of the said vesicles in a range of values corresponding to the size of the pores of the said membrane.

2. Process according to claim 1, wherein, after normalisation by extrusion, the polydispersivity index of the vesicles is not higher than 4.

3. Process according to claim 1, wherein the suspension of "normalized" liposomes is subjected to an ultracentrifugation or to an ultrafiltration in order to separate or concentrate the said vesicles of the said aqueous liquid, then these vesicles thus separated or concentrated are redispersed in a new dispersion medium free from dissolved iodine, the effect of this operation being to reduce the proportion of non-encapsulated iodine.

4. Process according to claim 1, wherein, after normalisation, the size of at least 70% of the liposomic vesicles is between 0.2 and 2 µm.

5. Process according to claim 4, wherein the suspension of "normalized" liposomes is subjected to a microfiltration, the effect of this operation being to eliminate a residual quantity of liposomes of which the size is below the said range, and also to reduce the concentration of non-encapsulated iodine of the aqueous suspension agent.

6. Process according to claim 1, wherein the operation takes place at a temperature higher than the transition temperature of the lipids constituting the liposomic membrane, the result of these conditions being to increase the concentration of the encapsulated iodine.

7. Process according to claim 6, wherein this temperature is between 50° and 90° C.

* * * * *